United States Patent [19]
Luchansky et al.

[11] Patent Number: 5,610,012
[45] Date of Patent: Mar. 11, 1997

[54] DNA PROBES SPECIFIC FOR VIRULENT LISTERIA MONOCYTOGENES

[75] Inventors: John B. Luchansky, Madison, Wis.; Jianchi Chen, Tallahassee, Fla.

[73] Assignee: Wisconsin Alumni Research Foundation, Madison, Wis.

[21] Appl. No.: 225,473

[22] Filed: Apr. 8, 1994

[51] Int. Cl.$^6$ .............. C12Q 1/68; C12P 19/34; C07H 21/04; C07H 19/04
[52] U.S. Cl. .............. 435/6; 435/91.2; 536/24.3; 536/24.33; 536/26.6
[58] Field of Search ......... 435/6, 91.2; 536/24.3–24.33, 536/28.6

[56] References Cited

FOREIGN PATENT DOCUMENTS

WO93/22454  11/1993  WIPO.

OTHER PUBLICATIONS

Chen et al., Applied and Environmental Microbiology, 59: 4367–4370 1993.
Erlich et al. In PCR Technology Principles and Applications for DNA Amplification, Freeman and Co, N.Y., Chs 1 and 19 pp. 7–16, pp. 235–244 1992.
Archer et al, "Contemporary Issues: Diseases with a Food Vector," Clin Micro. Rev. 1: 377–398 1988.
Bean et al. "Foodborne Disease Outbreaks in the United States, 1973–1987: Pathogens, Vehicles and Trends," J. of Food Protection, 53: 804–817 1990.
Bjournson et al., "Isolation of Rhizobium Loti Strain-Specific DNA Sequences by Subtraction Hybridization," Appl. Envir. Microbiol, 54: 2852–2855 1988.
Bubert et al, "Homologous and Heterologous Regions within the iap Gene Allow Genus and Species–Specific Identification of Listeria, spp. by Polymerase Chain Reaction," Appl. Environ. Microbiol. 58: 2625–263R2 1992.
Chen et al. "Sequestering DNA Sequences Unique to Listeria Monocytogenes" In Abstracts of the 93rd General Meeting of the American Society for Microbiology; American Society for Microbiology, :Washington, DC; Abstract No. P–79, P345 1993.
Chen et al. "Isolation of Listeria Monocytogenes–Specific Nucleotide Sequences" Appl. Env. Microbiol 59: 4367–4370, 1993.
Cook et al, "The Use of Subtractive Hybridization to Obtain a DNA Probe Specific for Pseudomonas Solanacearum Race 3", Mol. Gen. Genet., 227: 401–410 1991.
Farber et al. "Listeria Monocytogenes, A Food Borne Pathogen," Microbiol. Rev. 55:476–511 1991.
Goulet et al. "Epidemie de Listeriose en France Bilan Final Resultats de L'Enquete Epidemiologique," Bull Epidimol. Hebdomadaire, 4: 13–14 1993.
Kirkpatrick et al. "Cloning and Detection of DNA from a Nonculturable Plant Pathogenic Mycoplasmailike Organsim." Science 238: 177–200 1987.
Notermans et al, "Specific Gene Probe Detection of Biotyped and Serotyped Listeria Strains", Appl. Environ. Microbiol, 55, 902–906 1989.

(List continued on next page.)

Primary Examiner—W. Gary Jones
Assistant Examiner—Dianne Rees
Attorney, Agent, or Firm—Schwegman, Lundberg, Woessner & Kluth, P.A.

[57] ABSTRACT

An assay for detecting virulent *L. monocytogenes* is provided. This assay includes the steps of: contacting the nucleic acids of *L. monocytogenes* with a probe under conditions permitting hybridization; and detecting any probe that hybridizes to the nucleic acids. The probe used in this method includes a DNA sequence selected from a group consisting of a 0.9 kb HindIII-EcoRI fragment of plasmid pLUCH52, or a part thereof; a 1.1 kb HindIII-EcoRI fragment of plasmid pLUCH51, or a part thereof; and a 1.8 kb HindIII-EcoRI fragment of plasmid pLUCH44, or a part thereof).

22 Claims, 6 Drawing Sheets

OTHER PUBLICATIONS

Straus et al. "Genomic Subtraction for Cloning DNA Corresponding to Deletion Mutations," PNAS 87: 1889–1893 1990.

Welcher et al, "Selective Enrichment of Specific DNA, cDNA, and RNA Sequences Using Biotinylated Probes, Avidin and Copper–Chelate Agarose, Nucleic Acids Research", 14: 10027–10044 1986.

ISOLATE GENOMIC L. MONOCYTOGENES DNA
↓
CONSTRUCT LIBRARY IN E. COLI (pUC18)
↓
HYBRIDIZE GENOMIC LIBRARY WITH

| SUBTRACTER PROBE | VIRULENCE PROBE |
|---|---|
| (L. INNOCUA DNA) | (L. MONOCYTOGENES DNA) |

↓
RETAIN L. MONOCYTOGENES (+) AND L. INNOCUA (−) CLONES
↓
CONFIRM SPECIFICITY/VALIDATE PATHOGENICITY

FIG. 1

```
pLUCH51  CCCAACTTGCTAATTTATCGAACTTATTTATAGTCACTTTAACAAATCAAACAATTACCA  782
         | | |||  ||||||| | ||| | | | |||  - |  |||| ||| || -   ||
inlAB    CACCATTGGCTAATTTAACAAGAATCACCCAACTAGGGTTGAATGATCAAGCATGGACAA  2786 pLUCH51  ACCAACCCGTGTATTATCAAAATAATCTGTCGTTCCTAATGTAGTAAAGGTTCTTCTG    842
         |   |||  ||||| ||| ||  || ||  |||   |||  |||| ||| |||  |||
inlAB    ATGCACCAGTAAACTACAAAGCAAATGTATCCATTCCAAACGGTGAAAAATGTGACTG   2846 pLUCH51  GCGCGCCTATTGCACCTGCTACTATTAGGCGACAATGGAACATACGCTAGTCCAAATTTAA  902
         |||  ||| |||||||| |||||||||| |   ||  |||| |  |||||| | | ||
inlAB    GCGCTTTGATTGCACCTGCTATTAGCGATGGGTAGTTACGCAGAACCGGATATAA      2906 pLUCH51  CATGGAATTTAACTAGTTTTATTAATAATGTAGCTACACGTTTAACCAATCAGTCGCTT   962
         |||||||   || | ||| | |||| ||  || |||| |||||   ||  || | ||
inlAB    CATGGAACTTACCTAGTTATACAAATGAAGTAAGCTATACCTTTAGCCAACCTGTCACTA  2966 pLUCH51  TCAAAATACAACGGTTCCTTTCAGTTGGAACAGTTCCCAACCATTAA             1010
         | |||  ||  ||  | || ||  ||||||  |  | |   ||| |
inlAB    TTGGAAAGGAACGACAACATTTAGTGGAACCGTGACGCCAGCCACTTA            3014
```

FIG. 3

```
AAGCTTTCCGGTTTTTCTGAGCTGAAATTTTACTTCACTCGGATAAAACAGAAACAAAACCCCT
TTCAAAGACTATTCATCTACATTTTAGAAAAAAATTCGTTTAGGAATTGAGCAACTTCAAAGAA
AGAAATTGAGCAAGTCGGACAAGAATTGCGTATGCACCTAAAATCTATATTGCTTGTCTAGGCA
TGACGAAAACATTAGGAGAATATTTTCCAAAAGTCTGTTACATCGAAAAAGAATGTAGTTTTA
CCTATGATTCATTTATTATCGATATTTGCCACAAATGTTGAAAGAGATGATTTGATTATTATT
ATTTCTGAAAGCGGTGGCACCGAAAACACCCTTTCGCCTCGCGGAACATTTAAAATATAATTTAT
CGAATGTCATTGCGATTGTGAATAATCCAATGCCCAGATTCCCAATATGTGGAGACGATTATTT
ATGCTTCCAGTGAGGAGTTTGATGAAGATTCATTTAAACATCACGCCCCACTGTTAATTGTG
ATTGACTTGATTCTAAATATTTTTGAACAGCAAAAAAACTTATTTAAAATATATAAGGCAATT
TGCTTGACATGAAAACCCATTTCATCATTTAAATAATTCAGGCACTTGGAATGGAGTATCGGAGAG
TATGAAATTAGAGATGGGTATGCAAGATACTATCTTGTTTTGACCAAGATTTAGTTTGGGTATGAAAAAAGACA
TTTACATCGATAGAGACTATCTTGTTTTTGACCAAGATTTAGTTTGGGTATGAAAAAAGACA
AACGTTTCCAGTTGCAAATTAGGGCATATTGCGCTAGTTCGAGAAGAAGAGGAAATCATGCTAA
CATTTAGCTGCATTAAATATTAATATTGAATTC
```

```
GAATTCTGTATTTAAACTAGTTTTAATGGTAGCTGCTATTCTCGGTATTAGTCTATATGTAACGA
CAAGTCAAGGTGCGGAGGTTCCGCGCGAAAGCATTGCGCAGCAACCCAATTAATGTTATTTC
CCTGATCCGGCTCTTGCGAATGCAGTTAAAACAGGACTGGAAAATCTAATGTAACAGACGCTGT
TACGCTTGCAGATTTAGATGGAATAGCTACTTTATCAGCATTTAATACTGGAGTAACAACGATAG
AAGGAATACAATACTTAAATAATTTGATAGGGTTAGAACTTAAAGATAACCAAATAACTGATTTA
ACTCCTCTTAAAATTTAACGAAAATAACAGAGCTTGAATTATCTGGAAATCCGTTAAAAAATGT
GAGCGCGATTGCTGGGTTACAAAGCATTAAAACGCTAGATTTAACTTCTACACAAATTACAGATG
TGACTCCACTTGCAGGTCTCTTTCCAATTTGCAGGTATTATATTTGACCTCAATCAAATAACCAAT
ATAAGTCCGCTCGCAGGACTAACTAATTTACAATTATCAATCGGAAATAACCAAGTAAATGA
TTTAACCCCACTTGCTAATTTATCTAAACGACTTAAGAGTTCATTTGATGATAATAAAATAAGTG
ATATTTCGCCACTGCCACTTGCTAATTGCGAGTTAACCTTATAGAAGTTATTTATAGTCACTTAGT
GATGTCAGCCCACTGCTAATTTATCGAATTATTTATAGTCACTTTAACAAATCAAACAATTAC
CAACCAACCGTTATTATCAAATAATCTTGTCGTTCCTAATGTAGTAAAAGGTTCTTCTGGCG
CGCCTATTGCACCTGCTACTATTAGCGACAATGGAACATACGCTAGTCCAAATTAACATGGAAT
TTAACTAGTTTTATTAATAAATGTTAGCTACACGTTAACCAATCAGTCGCTTTCAAAATACAAC
GGTTCCTTTCAGTGGAACAGTTACCCAACCATTAACAGAAGCTT
```

```
AAGCTTCTGAAATGAAATTAGGAGGCCTAGCGGGAATCGCGCAACGGAAAAGCCACTGATTGATG
ATTACAACGCTGTTAGTTCTTATTACCTATAGTATCTATAAAGCAGACGATTTAAACACACCGCTT
GTGGAGCAAGAAGTTTCAACAGCGGCAGACTTTGAGAAGCACGTGTACTTTGATTTAACTAATAA
GCTCTTAGGACGAGGTTATTCTTATGTCATAAAATGCGGATGTTGTTTGAATGATAATTATGAA
GATCATCATATTGAAATTAATTCCGATACAATCCAAATCAAAAAGAAAAACCAACCGTTGAATA
CGAAATTTTAAGCCGCACAGGCGAGCGAAATTAAATTAAATGTATATGTAGAAGATGAGGAAGAA
TCTATCGTACCGGAACGCTTGAAATTACTAGTAGTACGACAGGCGGTAATGAGCAACTTCAAAGTGG
GAAAAATAATGTAACCTTATCACTTTCAAGCGAGGAACTACAACAATTAAAACAACAGGTGATT
ACATTATTACCAGCGGAAGTTCAGCCTATTTCAGATATTTTTATGCACGCAAACAGTTGGCAGCA
TTAAATACTATCCGCACCACAAGTTGGAGCTAAAATTGCCATGGATGCTTCAGGCAAATCAATGA
CTATCGCCCCAGAACCTAATGCAGTTGCAAAAACTTCTGTGATGAGAACTAAATATGATTTGAAA
GATAGCTGCAAAGCTCCAAACCAGATTATTCAATTACAAAATCTGGTCCTAATCAGCTAATACT
CAAAACCTTAATCTGCCTATAGGTAATATTTGGTTTGATAATTCTTATCAGCTAACCCTTGATAT
GAAAATGAATTATACAGAAAACAAAATCGATAACCAAAACCTAGCCAATAATTACTATCTATCTA
TTGGAATGGAGCGCTATTTGTTAGCTCTTTAAAGCGGAGCAGGTTTCGAACAACGAACAACGTAA
ATAGTGCGGATGTTTTTCAAAGTAACGAAAGCAAGCACCGATTCAGAAGGTAATATTTCCGGAGTT
ACATTTAAAAATATTTGGACTGATTCATTCAAATTAATCCGTCAAGCTGATGGAAGTTATGTACCAGAATTGAGCG
CGAGACTCCTGATTCATTCTTCTGTTGGACTAGTAACAGATGAAGCAGCTGGATCAAAAATCGATTTA
GTCGCTATGTTAGTTCTTCTGTTGGACTAGTAACAAGTTTCGGAAGCTATTTCTGTAAAAGCACTTAAGAGCCA
TATTCAACTCAGGAAAAATTAGAACAAGTTGTTTATGATAAACGCGTCAAAAATAGATGTTATTGGTGAG
GCTATTTCAGGCTGAGGAATATTAGTGTTTAAGAAAGATAACAAGAATGAACTGTTTGTAAATGTTTATAAAGC
GATAAAGACAATACAACGGTTAAGAGATTATCAATTCGGATTGATGACTACCAACACGCGATGTTTCTGTTA
AGATGGAACAACGCTCGTTAAATCAATTCGGATTATGTGTTAAAGTTGAAGGGAAATATGATTGTTAGATGGT
CAGAGCTTTCACCAGATTCAGATTATGTTGTTCAGACAATATTGAATATCGTCTGTACGATGCTGCAGACAATTT
AAAGGACGAAAAAGACAAAGTGTATTTTTCAGAGACAATTAAGACAATTAAGACAGAAAAAAGTTACCGAGTA
TGACTTCAACTGATTATTCATGGAATCCAGCATATGGTCAGCGAGCAATTAAAGGAAATATCCAT
TTTACTGATGAAAGTAGCGTATTAACAAATATTGAATATCGTCTGTACGATGCTGCAGACAATTT
CTTCCAATTTATCTAATTTAGTAGCTTTAGAGCAAGAGTTAGGCAATAAAACTCCCGTAGCTACA
TTTGATAATATGACAAATAGTCCAGAATTC
```

FIG. 6 ic sequence, i.e., DNA or RNA
DNA PROBES SPECIFIC FOR VIRULENT LISTERIA MONOCYTOGENES

STATEMENT OF GOVERNMENT RIGHTS

This invention was made with the support of the U.S. Government under United States Department of Agriculture NRICGP Grant No. 91-37201-6762. The Government has certain rights in the invention.

BACKGROUND OF THE INVENTION

There has been a steady increase in the incidence of diseases transmitted by food in the United States and growing concern over newly-emerging pathogens, notably *Listeria monocytogenes*. See D. L. Archer et al., *Clin. Micro. Rev.*, 1, 377 (1988); J. M. Farber et al., *Microbiol. Rev.*, 35, 476 (1991). *L. monocytogenes* is a ubiquitous, gram-positive, facultative anaerobic bacterium that is capable of growth over a wide temperature range (1°–45° C.), in high salt or nitrite concentrations, and at pH values between 4.8 and 9.6. See E. T. Ryser et al., *Listeria, Listeriosis, and Food Safety*; Marcel Dekker, Inc.: New York (1991). Although the first case of human listeriosis was reported over 60 years ago, it has only been in the last decade or so that *L. monocytogenes* has been firmly established as an important foodborne pathogen. During the 15 year period from 1973 through 1987, *L. monocytogenes* was second only to Salmonella in total deaths (70 and 88, respectively, of 274 total deaths) and first in death-to-case ratio (317 per 1,000 cases) in foodborne bacterial outbreaks of known outcome. See N. Bean et al., *J. Food Prot.*, 53, 804 (1990). As evidenced by the apparent worldwide increases in the incidence and cases of food-related listeriosis, including a recent French outbreak, *L. monocytogenes* remains a serious threat to human health. For example, see A. A. Goulet et al., *Bull. Epidemiol. Hebdomadaire*, 4, 13 (1993).

Despite advances in the isolation, enumeration, and control of *L. monocytogenes*, less progress has been made to distinguish illness-causing isolates from harmless isolates at the molecular level. Definition and characterization of genes of interest, including virulence factors, can be an arduous task, even if cloning and mutagenesis systems are operational. For example, the gene probe disclosed by S. Notermans et al., *Appl. Environ. Microbiol.*, 55, 902 (1989) was not specific for all *L. monocytogenes*. A typical commercially available detection assay for *L. monocytogenes* is based on a ribosomal RNA target-DNA probe and requires a critical mass of organism. As such, it is usually necessary to amplify the organism in culture before performing the assay. The process is further complicated, since associated phenotypes are difficult to select or score and/or all factors contributing to virulence have not been identified. For these reasons, a need exists for a method to reliably and rapidly differentiate virulent *L. monocytogenes* strains from otherwise phenotypically similar but avirulent varieties.

SUMMARY OF THE INVENTION

Accordingly, this invention aids in fulfilling these needs in the art by providing an assay for detecting in vitro in a sample the presence of virulent *Listeria monocytogenes* which can differentiate similar but avirulent Listeria strains as well as other bacterial strains. In a broad embodiment, the present assay comprises the steps of: contacting the nucleic acids of *L. monocytogenes* with a probe under conditions permitting hybridization; and detecting any probe that hybridizes to said nucleic acids. The probe used in this method includes a nucleotide sequence, i.e., DNA or RNA sequence, preferably a DNA sequence, selected from a group consisting of an about 0.9 kb HindIII-EcoRI fragment (preferably 877 base pair fragment) of plasmid pLUCH52, or a part thereof, as depicted in FIG. 2(A) (herein referred to as DNA sequence (1)); an about 1.1 kb HindIII-EcoRI fragment (preferably 1020 base pair fragment) of plasmid pLUCH51, or a part thereof, as depicted in FIG. 2(B) (herein referred to as DNA sequence (2)); and an about 1.8 kb HindIII-EcoRI fragment (preferably 1850 base pair fragment) of plasmid pLUCH44, or a part thereof, as depicted in FIG. 2(C) (herein referred to as DNA sequence (3)). The probes containing DNA sequences (1), (2), and (3) are referred to herein as probes (1), (2), and (3), respectively.

As used herein, a "part" of one of the DNA sequences (1),(2),or (3), of nucleotide sequences (1), (2), or (3), or of any probe based thereupon, is sufficiently long to provide for the selectivity of the in vitro detection of *L. monocytogenes*. The term "selectivity" or "specificity" of detection is defined by reference to the ability of probes derived from sequences (1), (2), or (3) to hybridize to DNA from strains of *L. monocytogenes*, while not hybridizing to DNA from other microorganisms, including other strains of Listeria, as shown in Table 1, hereinbelow, using the hybridization conditions set forth hereinbelow.

A preferred embodiment of the process of the present invention includes a step of making the nucleic acids of virulent *L. monocytogenes* accessible to the probe by fixing the nucleic acids to a solid support. Specifically, such a preferred method involves the steps of: depositing and fixing nucleic acids of the sample to be assayed for the presence of virulent *L. monocytogenes* on a solid support, so as to make the nucleic acids accessible to a probe; contacting the fixed nucleic acids with one of the probes listed above, i.e., sequences (1), (2), or (3), under conditions permitting hybridization; washing any hybridized probe to eliminate any non-hybridized probe; and detecting the hybridized probe. As used herein, the "hybridized probe" results from interaction of the probe with the fixed nucleic acids.

Probes (1), (2), and (3) have been found to be associated with intracellular DNA of virulent strains of *L. monocytogenes*. Each is capable of distinguishing such virulent microorganisms from avirulent strains of Listeria, which do not contain DNA that hybridizes with these probes under the conditions described hereinafter. Thus, the present invention also includes within its scope the following nucleotide sequences of the DNA probes (1), (2), and (3), as well as probes containing a detectable label, such as a chromophore or a radionuclide, conjugated or otherwise bonded to a nucleotide sequence of the invention. Specifically, the nucleotide sequences of the present invention are: an about 0.9 kb HindIII-EcoRI fragment of plasmid pLUCH52, or a part thereof (the DNA sequence of probe (1) referred to above, SEQ ID NO:1); an about 1.1 kb HindIII-EcoRI fragment of plasmid pLUCH51, or a part thereof (the DNA sequence of probe (2) referred to above, SEQ ID NO:2); and an about 1.8 kb HindIII-EcoRI fragment of plasmid pLUCH44, or a part thereof, (the DNA sequence of probe (3) referred to above, SEQ ID NO:3). This invention further provides a hybrid duplex molecule consisting essentially of a nucleotide sequence of the invention hydrogen bonded to a nucleotide sequence of complementary base sequence, such as DNA or RNA.

Further, this invention includes a kit for the detection of virulent *L. monocytogenes* in a sample derived from a foodstuff, a physiological material, or a clinical isolate. The kit includes a container having therein a probe comprising nucleotide sequences (1), (2), (3)(SEQ ID NO:1, SEQ ID NO:2, SEQ ID NO:3 ), or combinations thereof listed above. The kit also includes separate containers having therein control preparations of nucleic acid, e.g., derived from a nonvirulent strain of Listeria(negative control), or a virulent strain of Listeria(positive control). The kit also preferably includes means comprising instructions so that the art worker can carry out the assay of the present invention, such as a printed insert, a label, a tag, video cassette, or sotrod recording, and the like.

The present invention also provides oligonucleotide primers derived from the termini of the DNA sequences (1), (2), or (3)(including the complementary strands) (SEQ ID NO:1, SEQ ID NO:2, SEQ ID NO:3 ) that are effective to amplify and detect L. monocytogenes-specific DNA employing the techniques of polymerase chain reaction (PCR). For example, an oligonucleotide comprising about 7–30 bases proximal to the 5'-end of the single-stranded DNA of SEQ ID NO:1, SEQ ID NO:2, or SEQ ID NO:3, can be employed in concert with an oligonucleotide comprising about 7–30 bases proximal to the 3'-end of the sequences complementary to the single-stranded DNA of SEQ ID NO:1, SEQ ID NO:2, or SEQ ID NO:3, respectively, to amplify both strands of all, or of a substantial detectable portion of, the DNA inserts of FIG. 2(A)–(C), as described in more detail hereinbelow. The amplified double-stranded (ds) DNA product of PCR can be denatured and detected using probes comprising detectably labelled DNA (1), (2), or (3), or subunits thereof of at least about 7–10 nucleotides.

Nucleotide sequence data are deposited in GenBank under the accession numbers L16017 (lisM44; pLUCH44), L16018 (lisM51, pLUCH51), and L16019 (lisM52; pLUCH52).

BRIEF DESCRIPTION OF THE DRAWINGS

FIG. 1 is a schematic illustration of the subtracter probe hybridization (SPH) procedure used to isolate L. monocytogenes specific sequences.

FIG. 3 is a comparison of the nucleotide sequences of pLUCH51 (SEQ ID NO:4) and in inlAB (SEQ ID NO:5) by the best local aligment ming the BLAST network service.

FIG. 4 depicts the nucleotide sequence of the pLUCH52 fragment shown in FIG. 2(A) (SEQ ID NO:1).

FIG. 5 depicts the nucleotide sequence of the pLUCH51 fragment shown in FIG. 2(B) (SEQ ID NO:2).

FIG. 6 depicts the nucleotide sequence of the pLUCH44 fragment shown in FIG. 2(C) (SEQ ID NO:3).

DETAILED DESCRIPTION OF THE INVENTION

Figure 2A:
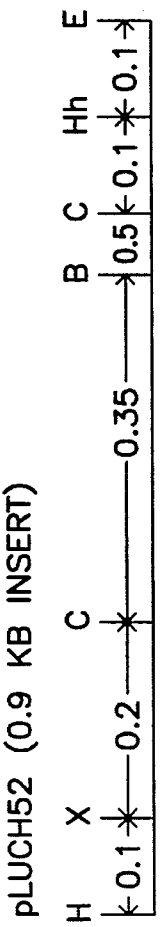
FIG. 2A–C is a diagram of selected restriction sites within three L. monocytogenes-specific fragments harbored by (A) pLUCH52, (B) pLUCH51, and (C) pLUCH44. 2A shows pLUCH52; 2B shows pLUCH51; 2C shows pLUCH44 Abbreviations: A, AscI; B, BccI; C, ClaI; E, EcoRI; Ec, EcoRII; H, HindIII; Hf, HinfI; Hh, HhaI; M, MluI; N, NlaIV; P, PstI; S, StuI; X, XmnI. Sites for restriction enzymes were confirmed by digestion and/or predicted from nucleotide sequence analyses.

Although as reported by D. A. Portnoy et al., *Infect. Immunol.*, 60, 1263 (1992), a few factors essential for the virulence of L. monocytogenes have been characterized, all factors involved in virulence have not yet been defined. See, for example, H. Hof et al., *Int. J. Food Microbiol.*, 16, 173 (1992). The isolation of additional virulence-associated and/ or L. monocytogenes-specific sequences by conventional methods could be cumbersome and time consuming. Furthermore, screening large numbers of putative avirulent mutants can be impractical when mouse lethality assays and/or cell lines are used.

The present assay was developed using subtracter probe hybridization ("SPH") to isolate virulent L. monocytogenes-specific sequences. The basic premise of SPH is that genes involved in the virulence of L monocytogenes are (presumably) absent in the closely related, but avirulent, subtracter DNA. Although similar in concept to the technique of genomic subtraction, i.e., subtractive hybridization, the advantages of SPH over that technique are that SPH is less technically demanding and the need to amplify subtracted or unique fragments which may be present in finite concentration is obviated. For general discussion of genomic subtraction, see D. Cook et al., *Mol. Gen. Genst.*, 227, 401 (1991) and A. J. Bjourson et al., *Appl. Environ. Microbiol.*, 54, 2852 (1988).

In general, the invention provides a method of detecting the presence of virulent Listeria monocytogenes in a sample including providing at least one nucleotide sequence probe, preferably a DNA probe, capable of selectively hybridizing to L. monocytogenes DNA to form detectable complexes. Detection is carried out with a sample under conditions which allow the probe to hybridize to L. monocytogenes DNA present in the sample to form hybrid complexes and detecting the hybride complexes as an indication of the presence of L. monocytogenes in the sample. This can be done in solution or using solid supports. For example, total DNA can be lysed onto membranes. The term "selectively hybridizing," as used herein, refers to DNA probe which hybridizes only to L. monocytogenes and not to avirulent Listeria strains, i.e., as shown on Table 1. However, for practical utility, it is not necessary that the present probes hybridize with every known strain of L. monocytogenes, since some are very rare in nature, or not highly toxic to humans. The sample can be comprised of the L. monocytogenes cells or a portion of the cells or cell contents enriched in L. monocytogenes nucleic acids, especially DNA. Hybridization can be carried out using conventional hybridization reagents. The particular hybridization conditions have not been found to be critical to the invention.

More particularly, and preferably, DNA sequence from L. monocygenes can be analyzed by Southern blotting and hybridization. The techniques used for the present invention are described in Sambrook et al., *Molecular Cloning: A Laboratory Manual* (Second Edition); Cold Spring Harbor Labortatory Press. New York (1989). DNA fragment can be separated on agarose gels and denatured in situ. The fragments can then be transferred from the gel to a water insoluble solid, porous support, such as a nitrocellulose filter, a nylon membrane, or an activated cellulose paper, where they are immobilized. For example, the Hybond® membrane commercialized by Amersham can be used. After prehybridization to reduce non-specific hybridization with the probe, the solid support is hybridized to a nucleic acid probe of the invention. The solid support is washed to remove unbound and weakly binding probe, and the resulting hybrid duplex molecule is examined. A convenient alterative approach is to hybridize oligonucleotides to the DNA denatured in the gel.

The amount of labelled probe which is present in the hybridization solution will vary widely, depending upon the nature of the label, the amount of the labelled probe which can reasonably bind to the filter, and the stringency of the hybridization. Generally, substantial excesses of the probe over a stoichiometric amount will be employed to enhance the rate of binding of the probe to the fixed DNA.

Various degrees of stringency of hybridization can be employed. The more severe the conditions, the greater the complementarity that is required for hybridization between the probe and the polynucleotide for duplex formation. Stringency can be controlled by temperature, probe concentration, probe length, ionic strength, time, and the like. Conveniently, the stringency of hybridization is varied by changing the polarity of the reactant solution. Temperatures to be employed can be empirically determined or determined from well known formulas developed for this purpose.

Unlike Southern hybridization where DNA fragments are transferred from an agarose gel to a solid support, the method of the invention can also be carried out by oligonucleotide hybridization in dried agarose gels. In this procedure, the agarose gel is dried and hybridization is carried out in situ using a nucleotide probe of the invention. This procedure is preferred where speed of detection and sensitivity may be desirable. The procedure can be carried out on agarose gels containing genomic or cloned DNA of *L. monocytogenes*.

In addition, the method of this invention can be carded out by transfer of *L. monocytogenes* DNA from gels to support matrices, e.g., membranes, by electroblotting or vacuum blotting, which may be desirable where time is of the essence because these techniques are typically faster than capillary blotting developed to transfer DNA from agarose gels. This method can be carried out in conjunction with UV-crosslinking. The polyacrylamide gel containing the samples to be tested is placed in contact with an appropriately prepared nylon filter. These are then sandwiched into an electroblotting apparatus and the DNA is transferred from the gel onto the filter using electric current. After a buffer rinse, the filter is ready to be prehybridized and hybridized or UV-crosslinked.

The method of the invention can be carded out using the nucleic acid probes of the invention for detecting virulent *L. monocytogenes* in biological samples, such as controlled cultures, or in foodstuffs.

The polynucleotide probe can be conjugated to a detectable label or a binding site for a detectable label. Useful labels include radioactive labels such as 32p, $^{3}H$, $^{14}C$, $^{125}I$ or the like. Any radioactive label can be employed which provides for an adequate signal and has sufficient half-life. Binding sites for detectable labels include ligands that can serve as specific binding members to labelled antibodies, a fluorescers, chemiluminescers, enzymes, antibodies which can serve as a specific binding pair member for a labelled ligand, and the like. The choice of the label will be governed by the effect of the label on the rate of hybridization and binding of the probe to the target DNA. It will be necessary that the label provide sufficient sensitivity to detect the amount of DNA available for hybridization.

In other embodiments, the probe can be labelled with biotin, which reacts with avidin to which is bonded chemical entity which, when the avidin is bonded to the biotin, renders the hybrid DNA complex capable of being detected, e.g., a fluorophore, which renders the hybrid DNA complex detectable fluorometrically; an electron-dense compound capable of rendering the hybrid DNA complexes detectable by an electron microscope; or one of a catalyst/substrate pair capable of rendering the hybrid DNA complexes enzymatically detectable.

Another detection method, which does not require the labelling of the probe, is the so-called sandwich hybridization technique. In this assay, an unlabelled probe, contained in a single-stranded vector, hybridizes to *L. monocytogenes* DNA, and a labelled, single-stranded vector, not containing the probe, hybridizes to the probe-containing vector, labelling the whole hybrid complex.

The sequences of the invention were derived by a dideoxynucleotide sequencing. The base sequences of the nucleotides are written in the 5'→3' direction. Each of the letters shown is a conventional designation for the following nucleotides:

A Adenine

G Guanine

T Thymine

C Cytosine

The nucleotides of the invention can be prepared by the formation of 3'→5' phosphate linkages between nucleoside units using conventional chemical synthesis techniques. For example, the well-known phosphodiester, phosphotriester, and phosphite triester techniques, as well as known modifications of these approaches, can be employed. Deoxyribonucleotides can be prepared with automatic synthesis machines, such as those based on the phosphoramidite approach, or other conventional techniques.

The nucleotides of the invention are in an isolated, purified form. For instance, the nucleotides are free of human blood-derived proteins, human serum proteins, bacterial food proteins, nucleotide sequences encoding these proteins, human tissue, and human tissue components. In addition, it is preferred that the nucleotides are free of other nucleic acids, extraneous proteins and lipids, and adventitious microorganisms, such as other bacteria and viruses.

This invention of course includes variants of the nucleotide sequences of the invention or serotypic variants of the probes of the invention exhibiting the same selective hybridization properties as the probes disclosed specifically herein.

The nucleotide sequences of the present invention can also be employed in a DNA amplification process known as the polymerase chain reaction (PCR). See, e.g., S., Kwok et al., *J. Virol.,* 61, 1690 (1987) and A. Bubert et al., *Appl. Environ, Microbiol.,* 58, 2625 (1992). DNA primer pairs of known sequence positioned 10–300 base pairs apart that are complementary to the plus and minus strands of the DNA to be amplified can be prepared by well known techniques for the synthesis of oligonucleotides. One end of each primer can be extended and modified to create restriction endonuclease sites when the primer is annealed to the single-stranded *L. monocytogenes* DNA. The PCR reaction mixture can contain the DNA, the DNA primer pairs, four deoxyribonucleoside triphosphates, $MgCl_2$, DNA polymerase, and conventional buffers. The DNA can be amplified for a number of cycles. It is generally possible to increase the sensitivity of detection by using a multiplicity of cycles, each cycle consisting of a short period of denaturation of the double stranded *L. monocytogenes* DNA at an elevated temperature followed by hybridization of the singlestranded DNA primers at a lower temperature, and polymerization with DNA polymerase.

Nucleotide sequences can also be used in a variety of probe or target amplification techniques, such as PCR, LCR, Q-β, 3SR, etc. Amplified sequences can be detected by several methods, including the use of a technique termed oligomer restriction (OR). Single-strand conformation polymorphism (SSCP) analysis can be used to detect DNA polymorphisms and point mutations in a variety of positions in DNA fragments. See, R. K. Saiki et al., *Bio/Technolol,* 3, 1008 (1985) and M. Orita et al., *PNAS USA,* 86, 2766

(1989). For example, after amplification, a portion of the PCR reaction mixture can be separated and subjected to hybridization with an end-labelled nucleotide probe, such as a $^{32}$P labelled adenosine triphosphate end-labelled probe. In OR, an end-labelled oligonucleotide probe hybridizes in solution to a region of the amplified sequence and, in the process, reconstitutes a specific endonuclease site. Thus, hybridization of the labelled probe with the amplified DNA sequences shown in FIGS. 4–6 yield a double-stranded DNA that is sensitive to selective restriction enzyme digestion. After restriction with an endonuclease, the resulting samples can be analyzed by gel electrophoresis, and autoradiograms of the portion of the gel with the diagnostic labelled fragment (e.g., 10–15 bases in length) in the autoradiogram indicates the presence of target sequences in the target organism.

Since it may be possible to increase the sensitivity of detection by using RNA instead of DNA as the nucleotide probe, this invention contemplates using RNA sequences that are complementary to the DNA probes described herein. The RNA probes may then form more stable hybrids with the DNA of interest.

The invention will be further described by reference to the following detailed examples. These examples are offered to further illustrate the various specific and preferred embodiments and techniques. It should be understood, however, that many variations and modifications may be made while remaining with the scope of the present invention.

EXPERIMENTAL EXAMPLE

In the following detailed examples, *L. monocytogenes* JBL1231 (clinical isolate; serotype 4b) and *Listeria innocua* JBL1007 (avirulent meat isolate; serotype 4bF6) were used as the probe and subtracter DNAs, respectively, for subtracter probe hybridization (SPH). In total, 206 listeriae were used to confirm the specificity of sequences obtained by SPH. Listeriae were propagated in brain heart infusion broth (Difco Laboratories, Inc., Detroit, Mich.) or on brain heart infusion agar (1.5%) plates. *Escherichia coli* HB101 was propagated in Luria-Bertani (LB) medium (See Sambrook et al., *Molecular Cloning: A Laboratory Manual* (Second Edition); Cold Spring Harbor Laboratory Press; Cold Spring Harbor: N.Y. (1982); hereinafter "Molecular Cloning"). All cultures were transferred twice at 37° C. prior to use.

Example 1

Manipulation, sequencing, and hybridization of DNA

The strategy for SPH is outlined in FIG. 1. To prepare a genomic library, *L. monocytogenes* JBL1231 genomic DNA was double digested with EcoRI and HindIII. The resulting EcoRI-HindIII fragments were ligated with EcoRI-HindIII-digested pUC18 (Sigma Chemical Co., St. Louis, Mo.) and electrotransformed into *E. coli* HB101. Plasmid DNA was first isolated from ampicillin-resistant (50 µg/ml) electrotransformants by using the modified boiling method of J. Chen et al., *Phytopathol.*, 82, 306 (1992); and then fractionated by agarose gel electrophoresis.

Total genomic DNA was also extracted from listeriae by using a modified boiling procedure of J. Chen et al., *Phytopathol.*, 82, 306 (1992). Briefly, log-phase cells were harvested by centrifugation and unsuspended in 1/20th the original volume of lysis buffer (2.5M LiCl, 62.5 mM EDTA, 0.4% Triton X-100, 50 mM Tris-HCl [pH 8.0], and 20 mg of lysozyme per ml). After overnight incubation at 37° C., the mixture was heated at 95° C. for 2 minutes, and the DNA was extracted with chloroform and precipitated with sodium acetate-ethanol (see "Molecular Cloning"). Restriction enzymes were purchased from Promega Corporation (Madison, Wis.) and used as described in the manufacturer's instructions.

For use as probes in hybridization experiments, total genomic DNAs from *L. monocytogenes* JBL1231 and *L. innocua* JBL1007 and/or plasmids pLUCH44, pLUCH51, and pLUCH52 were labelled with digoxigenin (Dig DNA Labelling and Detection Kit; Boehringer Mannheim Corporation, Indianapolis, Ind.). As described in further detail below, plasmids pLUCH44, pLUCH51, and pLUCH52 are three different derivatives of pUC18 that contain *L. monocytogenes*-specific sequences.

Nylon membranes (Magnagraph; Micron Separations, Inc., Westboro, Mass.) containing plasmids representing the *L. monocytogenes* JBL1231 genomic library were prehybridized and hybridized with digoxigenin-labelled *L. innocua* genomic DNA for 18 hours at 65° C. Membranes were washed once in 2× SSC-0.1% sodium dodecyl sulfate (SDS) for 30 minutes at room temperature and once in 0.5× SSC-0.1% SDS for 30 minutes at 65° C. (1× SSC is 0.15M NaCl plus 0.015M sodium citrate). Hybridization signals were detected colorimetrically by following the manufacturer's instructions.

After recording hybridization results, membranes were boiled twice in 1% SDS to remove *L. innocua* probe DNA and then reprobed with digoxigenin-labelled *L. monocytogenes* JBL1231 genomic DNA. Recombinant plasmids that hybridized with *L. monocytogenes* JBL1231 but not with *L. innocua* JBL1007 were retained for further analyses. When used as target DNA to confirm the specificity of sequences obtained by SPH, crude preparation of genomic DNA extracted from other listeriae were hybridized with pLUCH44, pLUCH51, and pLUCH52 as described earlier, but membranes were washed in 0.1×SSC, rather than 0.5× SSC, for the second wash.

The *L. monocytogenes* JBL1231 library was hybridized with labelled genomic DNA from *L. innocua* JBL1007 and then *L. monocytogenes* JBL1231. *L. monocytogenes* and *L. innocua* are highly similar phenotypically, but *L. innocua* is not a human pathogen. Of 300 clones initially screened (1.5-kb average insert=15% of the total genome), three clones (pLUCH44 [1,850-bp insert], pLUCH51 [1,020-bp insert], and pLUCH52 [877-bp insert] from the genomic library that hybridized with JBL1231 but not with JBL1007) were identified. As shown on Table 1, below, with the exception of *L. monocytogenes* ATCC 19114 (serotype 4a) and ATCC 19116 (serotype 4c), all three probes also hybridized with genomic DNA from 172 strains representing all other serotypes of *L. monocytogenes* but did not hybridize with genomic DNA from 32 strains representing all other Listeria species.

Regarding serotype 4a and 4c strains, pLUCH44 and pLUCH51 did not hybridize with the serotype 4a strain, whereas of the three plasmid probes tested, only pLUCH44 did not hybridize with the serotype 4c strain. A. Bubert et al., *Appl. Environ. Microbiol.*, 58, 2625 (1992) and S. Notennans et al., *Appl. Environ, Microbiol.*, 55, 902 (1989) have reported that serotype 4a strains did not hybridize with virulence probes composed of sequences from the *L. monocytogenes* iap or lma genes and that serotype 4a strains were less virulent in mice than strains of other serotypes. Also 4a and 4c strains are rare in nature. See for example, J.

McLauchlin, *J. Appl. Bacteriol.*, 63, 1–11 (1987) and S. Notermans et al., *Appl. Environ. Microbiol.*, 55, 902–906 (1989).

Likewise, as disclosed by I. Wesley et al., *Vet. Microbiol.*, 24, 341 (1990), serotype 4a and 4c strains failed to hybridize with a hly-specific probe.

TABLE 1

Hybridization of pLUCH44, pLUCH51, and pLUCH52 with Listeria strains

| Strains | Serotype | No. of strains hybridizing[a] | No. of strains tested |
|---|---|---|---|
| L. monocytogenes | 1 | 3 | 3 |
|  | 1/2a | 43 | 43 |
|  | 1/2b | 39 | 39 |
|  | 1/2c | 10 | 10 |
|  | 3 | 1 | 1 |
|  | 3a | 12 | 12 |
|  | 3b | 6 | 6 |
|  | 3c | 1 | 1 |
|  | 4 | 1 | 1 |
|  | 4a | 0 | 1 |
|  | 4b | 49 | 49 |
|  | 4c | 0 | 1 |
|  | 4d | 5 | 5 |
|  | 4e | 1 | 1 |
|  | "7" | 1 | 1 |
| Other Listeria spp. |  |  |  |
| L. grayi | ND[b] | 0 | 2 |
| L. innocua | 4, 6a, 6b | 0 | 10 |
| L. ivanovii | 5 | 0 | 6 |
| L. seeligeri | 1/2b | 0 | 6 |
| L. welshimeri | 6a, 6b | 0 | 8 |

[a]With the exception of serotype 4a and 4c strains, plasmids pLUCH44, pLUCH51, and pLUCH52 displayed identical hybridization behavior. Plasmids pLUCH44 and pLUCH51 did not hybridize with the serotype 4a strain, whereas only pLUCH44 did not hybridize with the serotype 4c strain.
[b]ND, not determined.

Example 2

Characterization of *L. monocytogenes*-specific sequences

Restriction maps were generated for the insert DNA within pLUCH44, pLUCH51, and pLUCH52 (i.e., *L. monocytogenes* sequences lisM44, lis M51, and lisM52, respectively), and are shown in FIG. 2.

The nucleotide sequences of *L. monocytogenes*-specific DNA fragments lisM52, lisM51, and lisM44 within pLUCH52, pLUCH51, and pLUCH44, respectively, were determined by ming Sequenase 2.0 (United States Biochemical Corporation, Cleveland, Ohio) and are shown in FIGS. 4 (SEQ ID NO:1), 5 (SEQ ID NO:2), and 6 (SEQ ID NO:3), respectively. Sequence information was analyzed by FASTA (W. R. Pearson et al., *PNAS USA*, 85, 2444 (1988)) and BLAST (S. F. Altshul et al., *J. Mol. Biol.*, 215, 403 (1990)) algorithms by ming the EMBL and NCBI network services, respectively.

As shown in FIG. 3 for pLUCH51, detailed comparisons to restriction maps and/or nucleotide sequence information for known Listeria sequences revealed that lisM51 exhibits about 60% identity with a 288-bp region of inlAB characterized by J. -L. Gaillard et al., *Cell*, 65, 1127 (1991). The latter gene encodes intemalin, a protein which mediates entry of *L. monocytogenes* into cells. In contrast, lisM44 and lisM52 are not appreciably similar to previously characterized *L. monocytogenes* sequences or any other sequences in the GenBank or EMBL repositories.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 877 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

```
AAGCTTTCCG  GTTTTTCTGA  GCTGAAATTT  TTACTTCACT  CGGATAAAAC  AGAAACAAAA      60

CCCCTTTCAA  AAGACTATTC  ATCTACATTT  TTAGAAAAAA  TTCGTTTAGG  AATTGAGCAA     120

CTTCAAAGAA  AGAAATTGAG  CAAGTCGCGA  CAAGAATTGC  GTATGCACCT  AAAATCTATA     180

TTGCTTGTCT  AGGCATGACG  AAAACATTAG  GAGAATATTT  TTCCAAAAGT  CTTGTTACAT     240

CGAAAAAGAA  TGTAGTTTTA  CCTATGATTC  ATTTATTATC  GATATTTTGC  CACAAATTGT     300

TGAAAGAGAT  GATTTGATTA  TTATTATTTC  TGAAAGCGGT  GGCACCGAAA  ACACCCTTTC     360

GCCTCGCGGA  ACATTTAAAA  TATAATTTAT  CGAATGTCAT  TGCGATTGTG  AATAATCCAA     420
```

| TGCCCAGATT | TCCCAATATG | TGGAGACGAT | TATTTATGCT | TCCAGTGAGG | AGTTTGATGA | 480 |
| AGATTCATTT | AAACATCATC | ACGCCCACT  | GTTAATTGTG | ATTGACTTGA | TTCTAAATAT | 540 |
| TTTTGAACAG | CAAAAAAAAC | TTATTTAAAA | TATTTTTATG | AAATTTGCTT | GACATGAAAC | 600 |
| CCATTTCATC | ATTTAAAACT | AATATATAAG | GCAATGAAGG | AGGCGAATGA | TATGAAATTA | 660 |
| GATGGGGTAT | GCAAGATTAA | TTCAGGCACT | TGGAATGGAG | TATCAATTCG | GAGAGTTTTA | 720 |
| CATCGATAGA | GACTATCTTG | TTTTTGACCA | AGATTTTAGT | TTGGGTATGA | AAAAAAGACA | 780 |
| AACGTTTCCA | GTTGCAAAAT | TAGGGCATAT | TGCGCTAGTT | CGAGAAGAAG | AGGAAATCAT | 840 |
| GCTAACATTT | AGCTGCATTA | ATATTAATAT | TGAATTC    |            |            | 877 |

( 2 ) INFORMATION FOR SEQ ID NO:2:

( i ) SEQUENCE CHARACTERISTICS:
        ( A ) LENGTH: 1019 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

| GAATTCTGTA | TTTAAACTAG | TTTTAATGGT | AGCTGCTATT | CTCGGTATTA | GTCTATATGT | 60 |
| AACGACAAGT | CAAGGTGCGG | AGGTTCCGCG | CGGAAAGCAT | TGCGCAGCAA | CCCCAATTAA | 120 |
| TGTTATTTTC | CCTGATCCGG | CTCTTGCGAA | TGCAGTTAAA | ACAGCGACTG | GAAAATCTAA | 180 |
| TGTAACAGAC | GCTGTTACGC | TTGCAGATTT | AGATGGAATA | GCTACTTTAT | CAGCATTTAA | 240 |
| TACTGGAGTA | ACAACGATAG | AAGGAATACA | ATACTTAAAT | AATTTGATAG | GGTTAGAACT | 300 |
| TAAAGATAAC | CAAATAACTG | ATTTAACTCC | TCTTAAAAAT | TTAACGAAAA | TAACAGAGCT | 360 |
| TGAATTATCT | GGAAATCCGT | TAAAAAATGT | GAGCGCGATT | GCTGGGTTAC | AAAGCATTAA | 420 |
| AACGCTAGAT | TTAACTTCTA | CACAAATTAC | AGATGTGACT | CCACTTGCAG | GTCTTTCCAA | 480 |
| TTTGCAGGTA | TTATATTTGG | ACCTCAATCA | AATAACCAAT | ATAAGTCCGC | TCGCAGGACT | 540 |
| AACTAATTTA | CAATACTTAT | CAATCGGAAA | TAACCAAGTA | AATGATTTAA | CCCCACTTGC | 600 |
| TAATTTATCT | AAACTAACGA | CTTTAAGAGC | TGATGATAAT | AAAATAAGTG | ATATTTCGCC | 660 |
| ACTTGCGAGT | TTACCTAACC | TTATAGAAGT | TCATTTGAAA | GATAATCAAA | TTAGTGATGT | 720 |
| CAGCCCACTT | GCTAATTTAT | CGAACTTATT | TATAGTCACT | TTAACAAATC | AAACAATTAC | 780 |
| CAACCAACCC | GTGTATTATC | AAAATAATCT | TGTCGTTCCT | AATGTAGTAA | AAGGTTCTTC | 840 |
| TGGCGCGCCT | ATTGCACCTG | CTACTATTAG | CGACAATGGA | ACATACGCTA | GTCCAAATTT | 900 |
| AACATGGAAT | TTAACTAGTT | TTATTAATAA | TGTTAGCTAC | ACGTTTAACC | AATCAGTCGC | 960 |
| TTTCAAAAAT | ACAACGGTTC | CTTTCAGTGG | AACAGTTACC | CAACCATTAA | CAGAAGCTT  | 1019 |

( 2 ) INFORMATION FOR SEQ ID NO:3:

( i ) SEQUENCE CHARACTERISTICS:
        ( A ) LENGTH: 1850 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

| AAGCTTCTGA | AATGAAATTA | GGAGGCCTAG | CGGGAATCGC | GCAACGGAAA | AGCCACTGAT | 60 |
| TGATGATTAC | AACGCTGTTA | GTTCTATTAC | CTATAGTATC | TATAAAGCAG | ACGATTTAAA | 120 |

| | | | | | | |
|---|---|---|---|---|---|---|
| CACACCGCTT | GTGGAGCAAG | AAGTTTCAAC | AGCGGCAGAC | TTTGAGAAGC | ACGTGTACTT | 180 |
| TGATTTAACT | AATAAGCTCT | TAGGACGAGG | TTATTCTTAT | GTCATAAAAT | GCGGATGTTG | 240 |
| TTTGGAATGA | TAATTATGAA | GATCATCATA | TTGAAATTAA | TTCCGATACA | ATCCAAATCA | 300 |
| AAAAAGAAAA | ACCAACCGTT | GAATACGAAA | TTTTAAGCCG | CACAGGCGAG | CGAAATTAAA | 360 |
| TTAAATGTAT | ATGTAGAAGA | TGAGGAAGAA | TCTATCGTAC | CGGGAACGCT | TGAAATTACT | 420 |
| AGTACGACAG | GCGGTAATGA | GCAACTTCAA | AGTGGGAAAA | ATAATGTAAC | CTTATCACTT | 480 |
| TCAAGCGAGG | GAACTACAAC | AATTAAAACA | ACAGGTGATT | ACATTATTAC | CAGCGGAAGT | 540 |
| TCAGCCTATT | TCAGATATTT | TTATGCACGC | AAACAGTTGG | CAGCATTAAA | TACTATCCGC | 600 |
| ACCACAAGTT | GGAGCTAAAA | TTGCCATGGA | TGCTTCAGGC | AAATCAATGA | CTATCGCCCC | 660 |
| AGAACCTAAT | GCAGTTGCAA | AAACTTCTGT | GATGAGAACT | AAATATGATT | TGAAAGATAG | 720 |
| CTGCAAAGCT | CCAAACCAGA | TTATTCAATT | ACAAAATCTG | GTCCTAATCA | ATTTAATACT | 780 |
| CAAACCTTA | ATCTGCCTAT | AGGTAATATT | TGGTTTGATA | ATTCTTATCA | GCTAACCCTT | 840 |
| GATATGAAAA | TGAATTATAC | AGAAACAAA | ATCGATAACC | AAAACCTAGC | CAATAATTAC | 900 |
| TATCTATCTA | TTGGAATGGA | GCGCTATTTG | TTAGCTCTTT | AAAGCGGAGC | AGGTTTCGAA | 960 |
| CAACGAACAA | CGTAAATAGT | GCGGATGTTT | TCAAAGTAAC | GAAAGCAAGC | ACCGATTCAG | 1020 |
| AAGGTAATAT | TTCCGGAGTT | ACATTAAAA | ATATTTGGAC | TGATAAGTAT | ATAGCTTATC | 1080 |
| GAAATGGTAT | TTTGATTAGT | AATAGCGAGA | CTCCTGATTC | ATTCAAATTA | ATCCGTCAAG | 1140 |
| CTGATGGAAG | TTATGTACCA | GAATTGAGCG | GTCGCTATGT | TAGTTTCTCT | GTTGGACTAG | 1200 |
| TAACAGATGA | AGCAGCTGGA | TCAAAAATCG | ATTTATATTC | AACTCAGGAA | AAATTAGAAC | 1260 |
| AAGTTTCGGA | AGCTATTTCT | GTAAAAGCAC | TTAAGAGCCA | GCTATTTCAG | GCTGAGGAAT | 1320 |
| ATTAGTGTTT | ATGATAAACG | CGTCAAAATA | GATGTTATTG | GTGAGGATAA | AGACAATACA | 1380 |
| ACGGTTAAGA | AAGATAACAA | GAATGAACTG | TTTGTAAATG | TTTATAAAGC | AGATGGAACA | 1440 |
| ACGCTCGTTA | AATCAATTCG | GATTGATGGA | CTACCAACAC | GCGATGTTTC | TGTTACAGAG | 1500 |
| CTTTCACCAG | ATTCAGATTA | TGTTGTTAAA | GTTGAAGGGA | AATATGATTT | GTTAGATGGT | 1560 |
| AAAGGACGAA | AAAGACAAAG | TGTATTTTTC | AGAGACAATT | AAGACAGAAA | AAAGTTTACC | 1620 |
| GAGTATGACT | TCAACTGATT | ATTCATGGAA | TCCAGCATAT | GGTCAGCGAG | CAATTAAAGG | 1680 |
| AAATATCCAT | TTTACTGATG | AAAGTAGCGT | ATTAACAAAT | ATTGAATATC | GTCTGTACGA | 1740 |
| TGCTGCAGAC | AATTTCTTCC | AATTTATCTA | ATTTAGTAGC | TTTAGAGCAA | GAGTTAGGCA | 1800 |
| ATAAAACTCC | CGTAGCTACA | TTTGATAATA | TGACAAATAG | TCCAGAATTC | | 1850 |

( 2 ) INFORMATION FOR SEQ ID NO:4:

( i ) SEQUENCE CHARACTERISTICS:
        ( A ) LENGTH: 288 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:4:

| | | | | | | |
|---|---|---|---|---|---|---|
| CCCAACTTGC | TAATTTATCG | AACTTATTTA | TAGTCACTTT | AACAAATCAA | ACAATTACCA | 60 |
| ACCAACCCGT | GTATTATCAA | AATAATCTTG | TCGTTCCTAA | TGTAGTAAAA | GGTTCTTCTG | 120 |
| GCGCGCCTAT | TGCACCTGCT | ACTATTAGCG | ACAATGGAAC | ATACGCTAGT | CCAAATTTAA | 180 |
| CATGGAATTT | AACTAGTTTT | ATTAATAATG | TTAGCTACAC | GTTTAACCAA | TCAGTCGCTT | 240 |
| TCAAAAATAC | AACGGTTCCT | TTCAGTTGGA | ACAGTTCCCA | ACCATTAA | | 288 |

( 2 ) INFORMATION FOR SEQ ID NO:5:

( i ) SEQUENCE CHARACTERISTICS:
        ( A ) LENGTH: 288 base pairs
        ( B ) TYPE: nucleic acid
        ( C ) STRANDEDNESS: double
        ( D ) TOPOLOGY: linear ( i i ) MOLECULE TYPE: DNA 1

( x i ) SEQUENCE DESCRIPTION: SEQ ID NO:5:

```
CACCATTGGC  TAATTTAACA  AGAATCACCC  AACTAGGGTT  GAATGATCAA  GCATGGACAA      60

ATGCACCAGT  AAACTACAAA  GCAAATGTAT  CCATTCCAAA  CACGGTGAAA  AATGTGACTG     120

GCGCTTTGAT  TGCACCTGCT  ACTATTAGCG  ATGGCGGTAG  TTACGCAGAA  CCGGATATAA     180

CATGGAACTT  ACCTAGTTAT  ACAAATGAAG  TAAGCTATAC  CTTTAGCCAA  CCTGTCACTA     240

TTGGAAAAGG  AACGACAACA  TTTAGTGGAA  CCGTGACGCA  GCCACTTA                   288
```

Figure 2B:
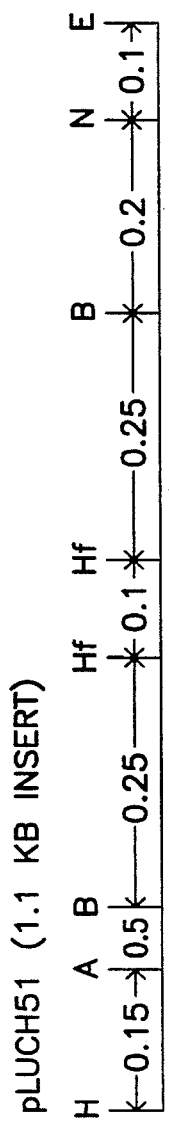
Figure 2C:
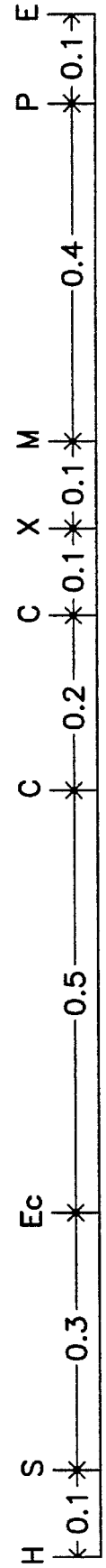

What is claimed is:

1. A method for detecting the presence of *Listeria monocytogenes* in vitro in a sample suspected of containing nucleic acids from *L. monocytogenes*, comprising:

(a) contacting the nucleic acids of the sample with a probe under conditions permitting hybridization; and (b) detecting any probe that hybridizes to said nucleic acids; wherein said probe is DNA selected from a group consisting of an about 0.9 kb HindIII-EcoRI fragment of plasmid pLUCH52 or a part thereof, as depicted in FIG. 2(A); an about 1.1 kb HindIII-EcoRI fragment of plasmid pLUCH51 or a part thereof, as depicted in FIG. 2(B); and an about 1.8 kb HindIII-EcoRI fragment of plasmid pLUCH44 or a part thereof, as depicted in FIG. 2(C); wherein said part is sufficiently long to provide for the selectivity of the in vitro detection of *L. monocytogenes* DNA.

2. The method of claim 1 wherein the probe further includes a detectable label or a binding site for a detectable label.

3. The method of claim 1 further including a step of depositing and fixing nucleic acids of the sample to be assayed for the presence of *L. monocytogenes* on a solid support, so as to make the nucleic acids accessible to the probe, prior to contacting the nucleic acids of the sample with the probe; and a step of washing the solid support to eliminate any non-hybridized probe prior to detecting the hybridized probe.

4. The method of claim 3 wherein the probe further includes a detectable label or a binding site for a detectable label.

5. The method of claim 4 wherein the probe comprises a radioactive enzymatic, fluorescent or luminescent label.

6. The method of claim 4 wherein the probe is bonded to a binding site for a detectable antibody.

7. The method of claim 1 wherein the probe is DNA selected from a group consisting of SEQ ID NO:1, SEQ ID NO:2, and SEQ ID NO:3.

8. A *Listeria monocytogenes*-specific DNA molecule which is an about 0.9 kb HindIII-EcoRI fragment of plasmid pLUCH52 or a part thereof; wherein said part is sufficiently long to provide for the selectivity of the in vitro detection of *L. monocytogenes* DNA.

9. The *Listeria monocytogenes*-specific DNA molecule of claim 8 which is SEQ ID NO:1.

10. A *Listeria monocytogenes*-specific DNA molecule which is an about 1.1 kb HindIII-EcoRI fragment of plasmid pLUCH51 or a part thereof; wherein said part is sufficiently long to provide for the selectivity of the in vitro detection of *L. monocytogenes* DNA.

11. The *Listeria monocytogenes*-specific DNA molecule of claim 10 which is SEQ ID NO:2.

12. A *Listeria monocytogenes*-specific DNA molecule which is an about 1.8 kb HindIII-EcoRI fragment of plasmid pLUCH44 or a part thereof; wherein said part is sufficiently long to provide for the selectivity of the in vitro detection of *L. monocytogenes* DNA.

13. The *Listeria monocytogenes*-specific DNA molecule of claim 10 which is SEQ ID NO:3.

14. A DNA probe selected from a group consisting of an about 0.9 kb HindIII-EcoRI fragment of plasmid pLUCH52 or a part thereof, as depicted in FIG. 2(A); an about 1.1 kb HindIII-EcoRI fragment of plasmid pLUCH51 or a part thereof, as depicted in FIG. 2(B); and an about 1.8 kb HindIII-EcoRI fragment of plasmid pLUCH44 or a part thereof, as depicted in FIG. 2(C); wherein said part is sufficiently long to prove for the selectivity of the in vitro detection of *L. monocytogenes* DNA.

15. The DNA probe of claim 14 further including a detectable label or a binding site for a detectable label.

16. The DNA probe of claim 15 wherein the detectable label is a radioactive, enzymatic, fluorescent or luminescent label.

17. The DNA probe of claim 14 wherein the DNA sequence is bonded to a binding site for a detectable antibody.

18. A kit for the in vitro detection of *Listeria monocytogenes* in a sample comprising:

(a) a container having therein a probe; wherein said probe is DNA selected from a group consisting of an about 0.9 kb HindIII-EcoRI fragment of plasmid pLUCH52 or a part thereof, as depicted in FIG. 2(A); an about 1.1 kb HindIII-EcoRI fragment of plasmid pLUCH51 or a part thereof, as depicted in FIG. 2(B); and an about 1.8 kb HindIII-EcoRI fragment of plasmid pLUCH44 or a part thereof, as depicted in FIG. 2(C); wherein said part is sufficiently long to provide for the selectivity of the in vitro detection of DNA from virulent strains of *L. monocytogenes*; and (b) a container having therein a control preparation of nucleic acid.

19. The kit of claim 18 wherein the sample is derived from a foodstuff, a physiological material, or a clinical isolate.

20. The kit of claim 18 which further comprises means comprising instructions for employing the kit for the in vitro detection of virulent strains of *L. monocytogenes*.

21. An oligonucleotide primer effective to amplify *L. monocytogenes* specific DNA in a polymerase chain reaction, wherein the primer is complementary with a nucleotide sequence at a terminus of a DNA molecule selected from a group consisting of an about 0.9 kb HindIII-EcoRI fragment of plasmid pLUCH52 or a part thereof, as depicted in FIG. 2(A); an about 1.1 kb HindIII-EcoRI fragment of plasmid pLUCH51 or a part thereof, as depicted in FIG. 2(B); and an about 1.8 kb HindIII-EcoRI fragment of plasmid pLUCH44 or a part thereof, as depicted in FIG. 2(C); wherein said part is sufficiently long to provide for the selectivity of the in vitro detection of *L. monocytogenes* DNA.

22. The oligonucleotide primer of claim 21 having about 7–30 nucleotides.

* * * * *